US005341215A

United States Patent [19]
Seher

[11] Patent Number: 5,341,215
[45] Date of Patent: Aug. 23, 1994

[54] METHOD AND APPARATUS FOR DETECTING THE PRESENCE AND/OR CONCENTRATION OF BIOMOLECULES

[75] Inventor: Jens-Peter Seher, Stuttgart, Fed. Rep. of Germany

[73] Assignee: Hewlett-Packard Company, Palo Alto, Calif.

[21] Appl. No.: 889,629

[22] Filed: May 28, 1992

[30] Foreign Application Priority Data

Jun. 8, 1991 [EP] European Pat. Off. ........ 91109430.8

[51] Int. Cl.$^5$ .......................... G01N 21/00; C12M 1/34
[52] U.S. Cl. ................................. 356/445; 422/82.08; 422/82.11; 422/82.09; 435/3; 435/291; 435/808; 436/165; 436/172
[58] Field of Search ..................... 356/445; 422/82.05, 422/82.08, 82.09, 82.11, 4; 435/287, 291, 808, 321, 174, 3; 436/165, 172

[56] References Cited

U.S. PATENT DOCUMENTS

| | | | |
|---|---|---|---|
| 4,765,737 | 8/1988 | Harris et al. | 356/336 |
| 4,844,613 | 7/1989 | Batchelder et al. | 422/82.05 |
| 4,889,427 | 12/1989 | Von Veen et al. | 472/82.11 |
| 4,979,821 | 12/1990 | Schutt et al. | 356/246 |
| 5,017,009 | 5/1991 | Schutt et al. | 358/338 |
| 5,055,265 | 10/1991 | Finlan | 422/82.05 |

FOREIGN PATENT DOCUMENTS

| | | |
|---|---|---|
| 0286195 | 10/1988 | European Pat. Off. . |
| 0305109 | 3/1989 | European Pat. Off. . |
| 0353937 | 2/1990 | European Pat. Off. . |
| 8807202 | 9/1988 | World Int. Prop. O. ........ 356/445 |

OTHER PUBLICATIONS

Daniels, P. B., et al, "Surface Plasmon Resonance Applied to Immunosensing", Sensors and Actuators, 15 (1988), pp. 11-18.
Fontana, E., et al., "Surface Plasmon Immunoassay", Applied Optics, vol. 29, No. 31, Nov. 1, 1990, pp. 4694-4704.
Matsubara, K., et al., "Multilayer System for a High-- Precision Surface Plasmon Resonance Sensor", Optics Letters, vol. 15, No. 1, Jan. 1, 1990, pp. 75-77.
Sutherland, R. M., et al., "Optical Detection of Antibody-Antigen Reactions at a Glass-Liquid Interface", Clinical Chemistry, vol. 30, No. 9, 1984, pp. 1533-1538.
Kooyman, R. P. H., et al., "Vibrating Mirror Surface Plasmon Resonance Immunosensor", Analytical Chemistry, vol. 63, No. 1, Jan. 1, 1991, pp. 83-85.
Sun, X., et al., "Experimental Studies on Biosensing by SPR", Japanese Journal of Applied Physics, vol. 28, No. 9, Sep. 1989, pp. 1725-1727.
Badley, R. A., et al., "Optical Biosensors for Immunoassays: The Fluorescence Capillary-Fill Device", Phil. Trans. R. Soc. Lond. B 316 (1987), pp. 143-160.
Kooyman, R. P. H., et al., "Surface Plasmon Resonance Immunosensors: Sensitivity Considerations", Analytica Chimica Acta, 213 (1988), pp. 35-45.

Primary Examiner—Robert J. Warden
Assistant Examiner—T. A. Trembley

[57] ABSTRACT

A method and apparatus for detecting the presence and/or concentration of biomolecules, in particular DNA, by providing a boundary surface between an optically denser medium and an optically rarer medium. Biomolecules adsorb to the boundary surface and alter the characteristics of impinging light. The method and apparatus use surface plasmon resonance (SPR) to excite the biomolecules. The angle of incidence of the impinging light is maintained at the angle at which SPR occurs, thereby controlling the energy transferred to the biomolecules. The energy transferred to the biomolecules causes the biomolecules to generate excitation light which is reflected and monitored at the boundary surface. The angle of incidence is controlled by rotating a desk such that the intensity of the reflected light is always maintained at a minimum which ensures that the angle of incidence is equal to the angle at which SPR occurs.

34 Claims, 6 Drawing Sheets

METHOD AND APPARATUS FOR DETECTING THE PRESENCE AND/OR CONCENTRATION OF BIOMOLECULES

FIELD OF THE INVENTION

The present invention relates to a method and apparatus for detecting biomolecules. In particular, the present invention relates to detecting DNA by irradiating a boundary surface with visible light causing surface plasmon resonance and detecting excitation energy reflected by the DNA molecules.

BACKGROUND OF THE INVENTION

Several methods for the detection of biomolecules, in particular of low concentration in a liquid, are known in the art. One method is based on so-called evanescent waves. The biomolecules to be detected are in a liquid solution and are brought into close contact with the surface of a medium, (e.g. glass), which is optically denser than the liquid used. This may be performed by adsorption of the biomolecules to complementary biomolecules immobilized on the glass surface. The biomolecules to be detected are marked with a fluorescent compound. Such may either be performed directly (i.e., by means of chemical binding between the biomolecule and the fluorescent substance), or in that biomolecules labelled with a fluorescent dye and immobilized or chemically bound to a part of the detection apparatus compete with the biomolecules to be detected; i.e., the unknown biomolecule releases a fluorescent biomolecule, which in turn adsorbs to the complementary biomolecule immobilized on the glass surface. The latter process is described in Badley, R. A., et al., "Optical Biosensors For Immunoassays: The Fluorescence Capillary-fill Device", Phil. Trans. R. Soc. Lond. B 316 (1987), pp. 143–160.

Monochromatic light, from a laser source or a filtered flash lamp, strikes the boundary surface between the optically denser medium (e.g., glass) and the optically rarer medium (e.g., an aqueous solution). The light beam is incident from the optically denser medium, and the angle of incidence is equal to or larger than the critical angle so that total internal reflection occurs. When such happens, an evanescent wave is created in the optically rarer medium (aqueous solution); this evanescent wave penetrates a fraction of a wavelength into the optically rarer medium. The electric field amplitude of the evanescent wave is largest at the boundary surface and decays exponentially with the distance from the interface.

Due to the limited depth of penetration of the evanescent wave, such wave is suited to monitor the presence of biomolecules at the boundary surface. It causes the fluorescent appendix of the biomolecules to emit light of a wavelength longer than the incident wavelength (this is effectively how fluorescence is defined). The fluorescence signal can be measured directly by monitoring the scattered light, or by measuring the light coupled back into the optically denser medium.

It is understood that the above technique is not limited to adsorption to a glass/aqueous solution interface. Instead, other materials may be used as well. It is further possible to use other effects than fluorescence which shifts the wavelength of the incident light to larger wavelengths, (e.g., phosphorescence or absorbance). In the latter case, even unlabelled biomolecules may be detected. The general method of detection is based on measuring a refractive index change caused by the presence of the biomolecules monitored by the refracted or reflected light, or, in other words, by the deviation of the angle of the reflected or refracted light. It is also known in the art to direct the incident light such that it is reflected multiple times in a waveguide, so that it strikes the boundary surface multiple times, see e.g., Sutherland, Ranald M. et al., "Optical Detection of Antibody-Antigen Reactions at a Glass-Liquid Interface", Clin. Chem. 30/9 (1984), p. 1533–1538.

Another technique for the detection of biomolecules is based on so-called surface plasmon resonance (SPR). This method requires a thin metal film, layer or coating (in more general terms, a conductive or semiconductive layer) between the glass and the liquid solution. Incident light, if impinging at a certain angle, causes surface modes (TE and/or TM modes) associated with collective electron oscillations to propagate along the interface between the metal film and the optically rarer medium (e.g., liquid solution). The incident light is usually coupled into the metal film by means of a prism or a grating. At a specific wavelength or angle, resonance occurs resulting in a sharp minimum or dip of reflectivity. The resonance condition is dependent upon the optical characteristics of the metal film, its thickness, the refractive indices of the dielectrics on either side of it (if any) and the angle of the incident light.

The first two of these characteristics remain basically unchanged in a given apparatus for performing surface plasmon resonance. However, the refractive index of the optically rarer medium varies with the amount of biomolecules bound or adsorbed to its surface. This is the property to be monitored.

In order to detect the presence and the amount of adsorbed biomolecules, either the variation in reflectivity at a given angle of incident light may be monitored, or the resonance shift (the reflectivity minimum is shifted to a different angle of incidence upon the presence of biomolecules) may be observed.

Surface plasmon resonance may be caused either by a metal grating, or by an evanescent wave resulting from total internal reflection (see above).

For further details of the surface plasmon resonance technique, reference is particularly made to Daniels, P. B. at al., "Surface Plasmon Resonance applied to Immunosensors, Sensors and Actuators", 15 (1988), p 11–18, and Kooyman, R. P. H. et al., "Surface Plasmon Resonance Immunosensors: Sensitivity Considerations", Analytica Chimica Acta, 213 (1988), p. 35–45.

Prior art surface plasmon techniques used the change of the refractive index caused by the biomolecules in order to detect their presence and/or their concentration. However, it is also known in the art to use the evanescent wave associated with surface plasmons to excite fluorescence or phosphorescence in an immunoassay, as described in EP-A-353 937.

A general problem in applying surface plasmon resonance is that the biomolecules may be "overexcited", i.e. too much energy is transmitted from the incident electromagnetic wave to the biomolecules. In such case, the biomolecules may bleach out, i.e., they alter their characteristics and their physical behavior, such that they may be no longer detectable. It will be appreciated that this effect impairs the results of the measurement.

The problem is that there is no control of the amount of energy "pumped" into the biomolecules. Of course, the energy emitted by the source of p-polarized electromagnetic waves is known and may be varied. However, the fraction of the total emitted energy pumped into the biomolecules is unknown (i.e., although the total emitted energy is known, the portion thereof passed on to the biomolecules is unknown). The reason is that, in prior art arrangements for the detection of biomolecules, the angle of incidence is not the exact angle at which surface plasmon resonance occurs (this angle will be called $\theta_{SPR}$ hereinafter) either because this angle cannot exactly be met, or, even if it were possible to adjust the apparatus exactly to $\theta_{SPR}$, this angle would be subject to drift caused by temperature effects, binding of unspecific molecules (i.e., molecules not subject to detection), changes at the metal/liquid interface, etc. Therefore, even the latter approach would lead to some deviation of the actual angle of incidence, with respect to the optimum angle $\theta_{SPR}$ for surface plasmon resonance.

The consequence of the actual angle of incidence not exactly corresponding to the optimum angle for surface plasmon resonance is that only a fraction of the total energy carried by the p-polarized electromagnetic waves is passed on to the biomolecules. On the other hand, and as outlined above, this fraction is unknown. Even if it were possible to determine the deviation of the actual angle versus the ideal angle precisely, such would not solve the problem, as the fraction of energy coupled into the biomolecules is not a well-defined function of the deviation.

Therefore, in prior art arrangements, effective control of energy coupled into the biomolecules has been substantially impossible. It is, of course, possible to reduce the total amount of energy emitted by the radiation source such that even a 100% energy coupling would not damage the biomolecules. However, assume that a deviation between the actual angle of incidence and the ideal angle $\theta_{SPR}$ for surface plasmon resonance causes a reduction of energy transmission of 75%. In such a case, the remaining energy pumped into the biomolecules would be insufficient for reliable measurements. On the other hand, if the total energy output of the radiation source were substantially increased, operation could be performed reliably even upon a very little energy coupling ratio, but a 100% coupling would then damage the biomolecules.

SUMMARY OF THE INVENTION

It is an objective of the present invention to provide a method for detecting the presence and/or the concentration of biomolecules of the kind described above for the excitation of surface plasmon resonance waves, wherein the method allows accurate control of the energy coupled into the biomolecules.

This object is solved in the present invention by monitoring the electromagnetic waves reflected at the boundary surface and detecting their intensity, and by controlling the angle of incidence $\theta$ of the impinging p-polarized electromagnetic waves depending on the intensity of the electromagnetic waves reflected at the boundary surface such that the intensity is substantially kept at a minimum corresponding to the occurrence of surface plasmon resonance (SPR).

The inventive method uses the fact that, if the actual angle of incidence corresponds to the ideal angle $\theta_{SPR}$ for surface plasmon resonance, then approximately 100% of the incident energy is coupled into the biomolecules. That is, the invention ensures that these angles are always maintained substantially equal. Then the total energy output from the radiation source is transmitted into the biomolecules. By controlling, the (known) energy transmitted from the radiation source, it is possible to determine accurately the amount of energy received by the biomolecules. The energy output of the radiation source may thus be precisely adjusted to the biomolecules to be detected, in order to ensure optimum detection without any damage of the biomolecules.

The ideal angle $\theta_{SPR}$ is kept by monitoring the intensity of the electromagnetic waves reflected at the boundary surface and controlling the angle of incidence such that the intensity is basically kept at its minimum. It should be noted that electromagnetic waves reflected at the boundary surface have usually another angle than the electromagnetic waves generated by the biomolecules by fluorescence, phosphorescence and similar effects. This is because the biomolecules adsorbed to the boundary surface alter the refractive index. Further, the "induced" radiation generated by fluorescence, phosphorescence etc. is of generally longer wavelength, or reduced frequency, as compared to the original electromagnetic wave. Therefore, two beams have to be monitored. A first beam originates from the biomolecules, wherein the intensity of this beam indicates their presence and/or concentration. A second beam is reflected at the boundary surface (the reflection angle of this second beam being equal to the angle of incidence). The intensity of this second beam is used to keep the angle of incidence at $\theta_{SPR}$, i.e., to meet the optimum of surface plasmon wave excitation.

The variation of the angle of incidence, is dependent on the intensity of the second beam and so that it is kept at a minimum, and may be affected in any convenient manner. In a preferred embodiment wherein the optically denser medium is a transparent prism (particularly a glass prism), such variation may be effected by rotation of a support carrying said transparent prism. However, there are further possibilities like moving the radiation source along a circular path around the center of the prism.

As outlined above, the general advantage of this method is that the energy of the radiation source may be accurately adapted to the biomolecules, in order to provide optimum measurements whilst avoiding damage of the biomolecules. However, there are further advantages of the inventive method. In particular, the apparatus is always kept at its optimum point of operation, thus saving energy. As approximately 100% of the energy is coupled into the biomolecules, no secondary effects caused by multiple reflected waves occur. Further, effects like temperature drift, adsorption of unspecific molecules, changes of the boundary surface etc. are eliminated. It is important to note that these advantages may be obtained even if the energy output of the source of radiation is not variable. Even in order to obtain the first advantage namely, controlled energy transfer to the biomolecules, a variable radiation source is not necessarily required, although such is provided in an advantageous embodiment of the invention.

In an advantageous embodiment of the invention wherein a transparent prism is carried by a rotatable support, said support is rotated in a first direction and then in a second direction opposite to said first direction in case an increase or a substantial increase in said intensity is detected, or in case a predetermined time period has expired. An increase or substantial increase of the reflected light is an indication that the ideal angle $\theta_{SPR}$ of surface plasmon resonance has moved to higher or lower values, so that the regions adjoining the previous angle should be searched for the new minimum. On the other hand, to ensure continuous proper operation, it is advantageous to scan the regions adjoining the present point of operation from time to time, even if no substantial increases have been noted.

In an alternative embodiment, the electromagnetic waves reflected at the boundary surface are monitored by several monitoring elements, e.g., an array sensor comprising elements sensitive to said electromagnetic waves such as photodiodes or phototransistors. A central sensing or monitoring element serves as a reference. It is a goal of this embodiment to have the minimum intensity of the reflected electromagnetic waves focused on this central element.

Even if the reflected beam is focused on the central element, the incident and the reflected waves do not merely oscillate strictly in a single plane, i.e., there are also lateral or stray waves. These are irradiated onto the boundary surface at an angle slightly different from the optimum angle $\theta_{SPR}$ for surface plasmon resonance. Sensing or monitoring elements arranged laterally with respect to the central element are used to record such stray waves. If the detection apparatus operates at its optimum point, i.e., at $\theta = \theta_{SPR}$, the intensity recorded by the lateral elements is therefore expected to be larger than the intensity of the central element. If, however, the intensity recorded by the lateral elements falls below the intensity recorded by the central element, this is an indication that the apparatus is no longer operating at $\theta = \theta_{SPR}$, either because of a misadjustment or because the optimum wavelength for surface plasmon resonance has moved, e.g., caused by temperature effects or due to the adsorption of unspecific molecules. Therefore, if this happens, a control signal is generated in order to readjust the equipment. It is understood that the above arrangement of a central and two lateral recording elements is for the purpose of illustration. For more accurate control, more lateral elements may be used, e.g., an array of 11 photodiodes. It is also possible to arrange the sensing elements in a 2-dimensional configuration rather than 1-dimensionally as described above.

Advantageously, the p-polarized electromagnetic waves are passed through a thin dielectric film before and/or after passing through said thin conductive film. Such dielectric film may, be arranged between a metal film to which the biomolecules adsorb, and a glass prism. Use of such dielectric layer sharpens the resonance peak and has other related advantages. Basically, dielectric layers of this kind have already been known in the art, (see e.g., EP-A-353 937).

In a further preferred embodiment, the optically rarer medium is a solvent in which said biomolecules are dissolved such that said biomolecules adsorb to, deposit on, or are physically or chemically bound to the optically rarer side of said boundary surface. That is, the biomolecules are present at the optically rarer side of the boundary surface. This is the usual (however not the only) way of detecting biomolecules. Several techniques may be used to establish contact between the biomolecules in solution and the boundary surface. These techniques, most of them well-known in the art, use various physical and/or chemical effects. The most common one is simple adsorption. However, more sophisticated ways like a competition process between the biomolecules to be detected and already present, marked biomolecules (see e.g., Badley, R. A. et al, "Optical Biosensors for Immunoassays: The Fluorescence Capillary-fill Device", Phil. Trans. R. Soc. Lond. B316, 143–160 (1987)) have also been used.

Advantageously, the inventive method uses biomolecules marked with a fluorescent, phosphorescent, chemiluminescent or electroluminescent substance. Such substances are excited by the surface plasmon wave and emit a radiation of reduced frequency, as compared to the frequency of the incident wave. The wave of reduced frequency is easier to detect than waves of the same frequency (the latter approach, namely to detect only the refractive index change caused by the biomolecules, i.e., to measure light of the same frequency as the frequency of the incident wave, has been used in most prior art publications). However, it has to be noted that the present invention is not restricted to the advantageous embodiment incorporating labelled biomolecules. Instead, measurements based on absorption, Raman spectroscopy and nonlinear effects may be performed by the method and apparatus according to the present invention as well.

If labelled biomolecules are used, the biomolecules to be detected (unknown biomolecules) may be directly labelled by a chemical binding with a fluorescent substance. However, there are also more sophisticated ways where the chemical structure of the unknown biomolecules need not be altered. Usually, such techniques employ the use of further labelled biomolecules. One such technique, namely a competition process between the unknown biomolecules and labelled biomolecules, has already been mentioned above. Instead, it is also possible to use complementary labelled biomolecules.

An advantageous embodiment based on such complementary labelled biomolecules will be described now.

According to this embodiment, the optically rarer side of said boundary surface is coated with capture molecules complementary to the unknown biomolecules. The solvent contains the unknown biomolecules as well as labelled biomolecules complementary to the unknown biomolecules in solution. That is, two kinds of complementary biomolecules are used. The first is the capture molecules (also referred to as "capture probe") immobilized on the boundary surface. The second kind are the molecules labelled, for example, with a fluorescent substance and dissolved in the solution (also referred to as "label probe"). The unknown biomolecules are also called "target probe".

During measurement, the target probe adsorbs to the capture probe. On the other hand, the label probe adsorbs to the target probe, such that its label is excited by the surface plasmon wave.

The above process is particularly useful if deoxyribonucleic acid (DNA) sequences are to be detected. In this case, a preferred embodiment of the inventive method operates as follows. A surface plasmon wave is excited, which in turn excites fluorescent labels. These fluorescent labels can be attached to the biomolecules under investigation or the label probe and will lead to a very sensitive and specific detection system.

To detect, for example, a specific DNA sequence ("target DNA"), it is proposed first to hybridize the single strand of this target DNA with its complementary synthetic strand in solution. The synthetic strand (label probe) has to be longer than 16 bases to guarantee its specificity and is prelabelled or prepared to be labelled afterwards. This target-label complex is then immobilized at the metal interface by hybridization to another complementary synthetic strand (capture probe), which is bound to the metal interface. By embedding the metal film layer between layers of different dielectrics one may optimize the strength of the evanescent wave as well as improve the binding of the capture probe. At a certain angle of incidence, the reflected beam will show a sharp dip, and this angle is quasi-identical with the angle of coupling maximum power into the sample volume with the labelled and immobilized target DNA. This sharp dip is used as a control value to define optimal conditions for maximum photon output of the fluorescent label; this, in turn, allows minimum excitation power, thereby reducing the possibility of photodestruction. To further improve the signal to noise ratio, a fluorescence label with a long decay rate and a large Stokes shift can be applied to decrease the influence of the intrinsic fluorescence and of the excitation light upon the detected surface plasmon signal. It is possible to couple a great amount of the fluorescence light which is emitted by the fluorescent molecule back into the denser medium. The advantage of such device is a complete separation between sample volume and optic path. In addition, the different dielectric layers and the metal layer can be deposited onto a thin coverglass, which itself is matched to the denser medium. Such modified coverglass may be used as a cheap and disposable device, and the light source and the detector may be integrated in the denser medium. The denser medium may advantageously also have the shape of a semicylindrical prism into which a wedge-shaped light beam with defined minimum and maximum angle of incidence can be coupled.

A suitable fluorescence label for the above process is, for example, a metal out of the rare earth elements. The long decay rate of these elements has the advantage that the emission is still detectable even after the decay of the intrinsic fluorescence, and the large Stokes shift will result in optical decoupling between excitation light, intrinsic fluorescence and emitted light.

In order to apply such fluorescence labels, proteins like biotin, digoxigenine or other suitable substances are inserted into the DNA strand. Such proteins bind specifically to molecules like avidin or antibodies which comprise, in turn, fluorescent and phosphorescent molecules.

A typical capture DNA, as well as a label DNA, is a synthetic oligonucleotide, complementary to the target DNA and comprising approximately 20 bases.

The present invention also relates to an apparatus operative to perform the above method. According to one aspect of the invention, such apparatus for the detection of the presence and/or concentration of biomolecules comprises: a source of electromagnetic waves, preferably in the spectrum of visible light, a polarizing means for p-polarizing the electromagnetic waves emitted by the source of electromagnetic waves, a means for directing the p-polarized electromagnetic waves through an optically denser medium onto the boundary surface between an optically denser and an optically rarer medium, a thin conductive or semiconductive film, preferably metal film, on the boundary surface, and first monitoring means for monitoring radiation reflected or generated by the biomolecules at the boundary surface, a second monitoring means for monitoring electromagnetic waves reflected at the boundary surface, an intensity detection means for detecting the intensity of the electromagnetic waves reflected at the boundary surface, a control means for controlling the angle of incidence of the impinging p-polarized electromagnetic waves dependent on the intensity of the electromagnetic waves reflected at the boundary surface such that the intensity is substantially kept at a minimum corresponding to the occurrence of surface plasmon resonance.

According to the inventive apparatus, the second monitoring means detects the electromagnetic waves reflected at the boundary surface. The intensity of the reflected electromagnetic waves is then used to control the angle of incidence. This is performed by the control means.

It would be known to those skilled in the art that the second monitoring means and the intensity detection means mentioned above may be integrated in one component, or both tasks may be performed by a common component. Likewise, the first and second monitoring means may be a common component. Such is particularly the case if absorbance is used to detect biomolecules; the angles of the electromagnetic waves reflected by the boundary surface, and the angles of the electromagnetic waves reflected by the biomolecules, differ then only slightly. However, in case fluorescence or phosphorescence is used, where there is a notable difference between the above angles, different monitoring means may be used.

In general, the first monitoring means, the second monitoring means and the intensity detection means may be combined in any suitable manner. For example, if the above angles differ only slightly, the same detector could be used to record the electromagnetic waves reflected from the boundary surface and the electromagnetic waves (e.g., light) emitted by the biomolecules. A diode array could be a suitable detector for such environment. Filters could be used as well.

There are various alternatives for controlling (or correcting) the angle of incidence. In a preferred embodiment, wherein the optically denser medium is a transparent prism (e.g., glass), such prism may be mounted on a rotatable support, wherein a motor (such as a stepper motor) rotates the support depending on the control signal generated by the control means. If the angle of incidence is rotated for $\Delta\theta$, then the second monitoring means is rotated for $2*\Delta\theta$. Therefore, it is advantageous to have a transmission means, such as a gear which rotates the second monitoring means for $2*\Delta\theta$ when the glass prism is rotated around $\Delta\theta$. Tables or desks performing this function are well-known in the art and commercially available.

However, it should be noted that there are further possibilities of changing the angle of incidence depending on the control signal, for example, by moving the radiation source along a circular path around the center of the prism or using an array of radiation sources, wherein only one of these sources is active (i.e., emitting) at a certain point in time, depending on the control signal.

There are also several advantageous ways of generating a control signal. One of these solutions (which may be realized in software) has already been described above, namely to search the regions adjoining the present point of operation for an intensity minimum. One way to perform such a search will be discussed in the detailed description. According to a further suitable solution, the second monitoring means comprises an array of monitoring elements, preferably photodiodes or phototransistors, with at least a central monitoring element and at least a lateral element at either side of said central monitoring element, wherein control signal generating means are provided generating at least a control signal if the intensity recorded by one of said lateral elements is lower than the intensity recorded by said central element, said control signal being fed to said control means.

As already outlined at the beginning, it is a major goal of the present invention to control exactly the amount of energy coupled into the biomolecules. As the invention ensures that the transmission rate is always approximately 100%, it is further advantageous to have an adjustable radiation source, in order to adapt its energy output to the biomolecules under investigation. However, if only one type of biomolecule will be examined, the radiation source need not be adjustable.

The above method and apparatus have proven especially useful and suited for the detection of deoxyribonucleic acid molecules. However, it will be appreciated that other kinds of biomolecules may be reliably detected by such method and apparatus as well.

BRIEF DESCRIPTION OF THE DRAWINGS

An embodiment of the invention will now be described, by way of a non-limiting example, with reference to the accompanying drawings, in which.

DETAILED DESCRIPTION OF THE INVENTION

Figure 1:
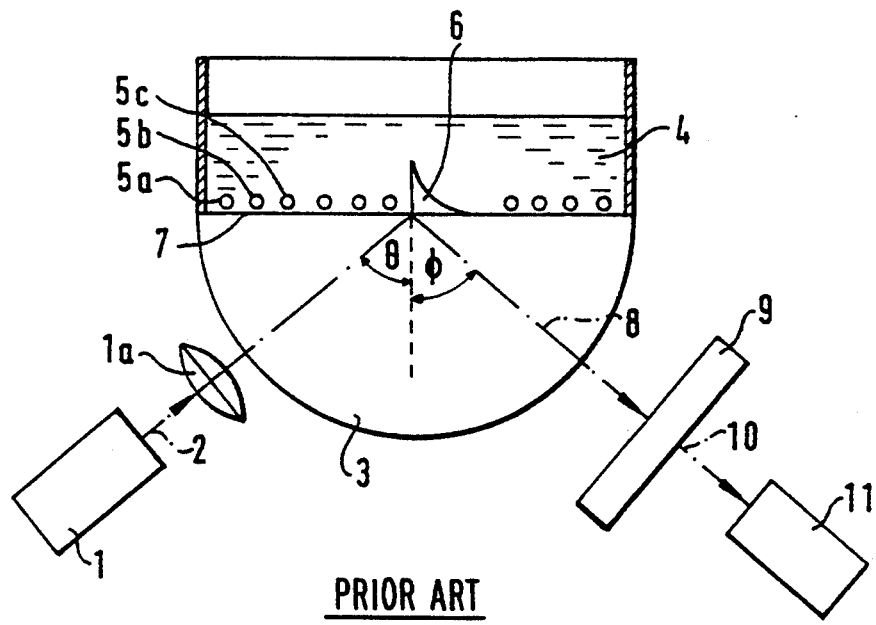
FIG. 1 depicts a prior art arrangement for exciting biomolecules to generate evanescent waves and for measuring the concentration of the biomolecules.

In a prior art arrangement shown in FIG. 1, a source of electromagnetic radiation, such as p-polarized light in the visible spectrum is provided. The light is fed (light ray 2) through a lens 1a into a semicircular glass prism 3. A solvent 4 contains dissolved DNA molecules (three of which are labelled 5a, 5b and 5c in FIG. 1) to be detected. Glass prism 3 acts, with reference to solvent 4, as the optically denser medium; the solvent is the optically rarer medium.

The angle of incidence $\theta$ is selected such that total internal reflection occurs, i.e., $\theta \geq \theta_{Cr}$ (Critical angle).

When total internal reflection occurs, an evanescent wave is created, which penetrates a fraction of a wavelength into the optically rarer medium (solvent 4). This evanescent wave is diagrammatically indicated at 6. Although there is no net flow of energy into solvent 4, the electric field amplitude of the evanescent wave 6 is largest at the boundary surface 7 between glass prism 3 and solvent 4 and decays exponentially with the distance from the boundary surface.

In FIG. 1, DNA molecules 5a to 5c are labelled with a fluorescent substance. Evanescent wave 6 excites the fluorescent substance, which in turn emits light of lower frequency (due to the losses), i.e., $\nu_{emitted} \leq \nu_{impinging}$ wherein $\nu_{emitted}$ indicates the frequency of the light emitted by the fluorescent substance, and $\nu_{impinging}$ indicates the frequency of the impinging light (reference number 2). One could also write $\nu_{emitted} = \nu_{impinging} - \Delta\nu$, wherein $\Delta\nu$ represents the losses in the fluorescent substance.

The light emitted by the fluorescent substance is then coupled back into glass prism 3, as indicated by light ray 8. Due to the different frequency, the angle of the emitted light $\phi$ is not exactly identical to the angle of incidence $\theta$ (It has to be noted that this is not "reflected" light in the common meaning of this term ). Light ray 8 then reaches an optical filter 9 which permits only light of frequency $\nu_{emitted}$ to pass, i.e., light not originating from fluorescence is blocked. The filtered light is fed (light ray 10) to a detector 11.

The intensity of the light impinging on detector 11 is now directly proportional to the amount of DNA molecules labelled with a fluorescent substance and adsorbed to boundary surface 7.

Figure 2:
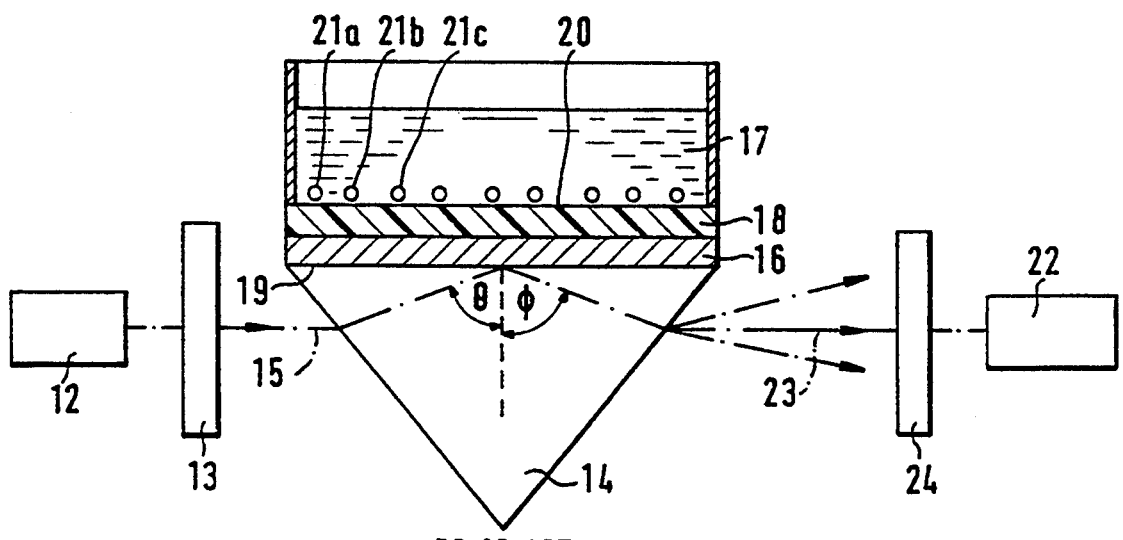
FIG. 2 shows a prior art arrangement for exciting a conductive or semiconductive medium thereby producing surface plasmon resonance (SPR) and for measuring the concentration of biomolecules.

FIG. 2 depicts a prior art arrangement for the excitation of biomolecules via surface plasmon waves. P-polarized light generated by radiation source 12 is fed to filter 13 and then to glass prism 14 (light ray 15). A major difference between the arrangements of FIGS. 1 and 2 is that a thin metal layer 16 is provided between glass prism 14 and solvent 17. Further, a dielectric layer 18 separates metal layer 16 from solvent 17 (although not shown in FIG. 2, a similar dielectric layer may be provided between metal layer 16 and glass prism 14).

If the incident light impinges on boundary surface 19 at an angle $\theta \approx \theta_{SPR}$, surface plasmon resonance (SPR) occurs, i.e. surface modes associated with collective electron oscillations in the metal film are exited. The surface plasmon wave is a "bound" wave (i.e., no energy is radiated) propagating along boundary surface 20 (the boundary surface to solvent 17). The surface plasmon wave propagates in metal film 16 as well as along the surface of solvent 17. Dielectric film 18 reduces the losses due to propagation in metal film 16.

Figure 3:
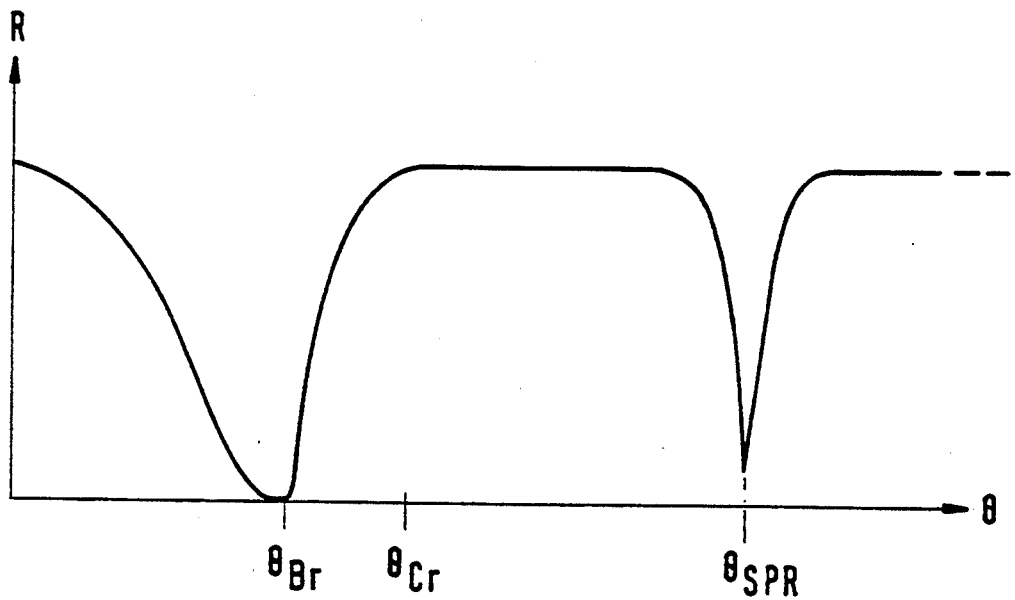
FIG. 3 is a diagram showing the reflectivity of p-polarized light.

In general, and as will be shown below, $\theta_{SPR} > \theta_{Cr}$. DNA molecules 21a to 21c adsorb to boundary surface 20, thereby altering the refractive index at the boundary surface. This change in the refractive index can be monitored by detector 22. The light ray to the detector is denoted as 23 in FIG. 2; this light ray passes through a further filter 24. The angle $\phi$ of the light fed to the detector is different from the angle of incidence $\theta$, due to the refractive index change caused by DNA molecules 21a to 21c, i.e., $\phi \neq \theta$ FIG. 3 depicts the reflectivity R of p-polarized light depending on the angle of incidence, $\theta$. At the critical angle $\theta_{Cr}$ (critical angle which is greater than the Brewster angle $\theta_{Br}$), total internal reflection occurs. At this angle, the reflectivity of p-polarized light is nearly 1. A sharp dip in reflectivity is observed at $\theta = \theta_{SPR}$. This is the angle of incidence where surface plasmon resonance occurs.

It will be noted that the minimum at $\theta = \theta_{SPR}$ is quite small. That is, in case the angle of incidence is further increased, i.e., $\theta > \theta_{SPR}$, no surface plasmon resonance will occur. The same is true for $\theta < \theta_{SPR}$.

Figure 4:
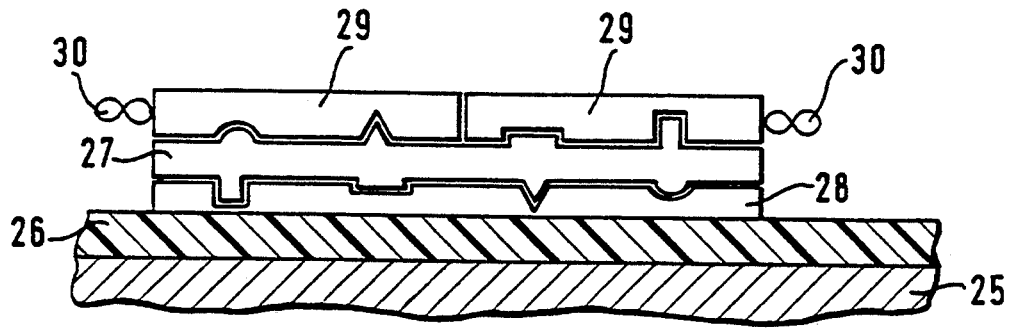
FIG. 4 depicts schematically the absorbance mechanism of DNA strands.

A basic approach to have DNA molecules adsorb to the boundary surface in the present invention is shown in FIG. 4. The metal film is labelled as 25 in this figure; 26 is the dielectric layer The "target DNA", i.e. the DNA to be detected, is shown as 27.

Dielectric layer 26 carries a "coating" of capture DNA 28. Capture DNA 28 is immobilized on dielectric layer 26 and of complementary structure with respect to target DNA 27.

During measurement, target DNA 27 as well as a further complementary DNA, namely label DNA 29, are dissolved in a solvent like water. Part of target DNA 27 hybridizes with label DNA 29 in solution. Thereafter, another part of target DNA 27 hybridizes with capture DNA 28, such that the whole complex is immobilized on the boundary surface. It is understood that the first hybridization (target DNA with label DNA) runs faster, namely in three dimensions in the solvent; the 2-dimensional hybridization target DNA/-capture DNA is slower.

Label DNA 29 is chemically bound to a fluorescent substance 30, in the way described above. The amount of fluorescent substance is thus a measure of the amount of target DNA in the solution.

Figure 5:
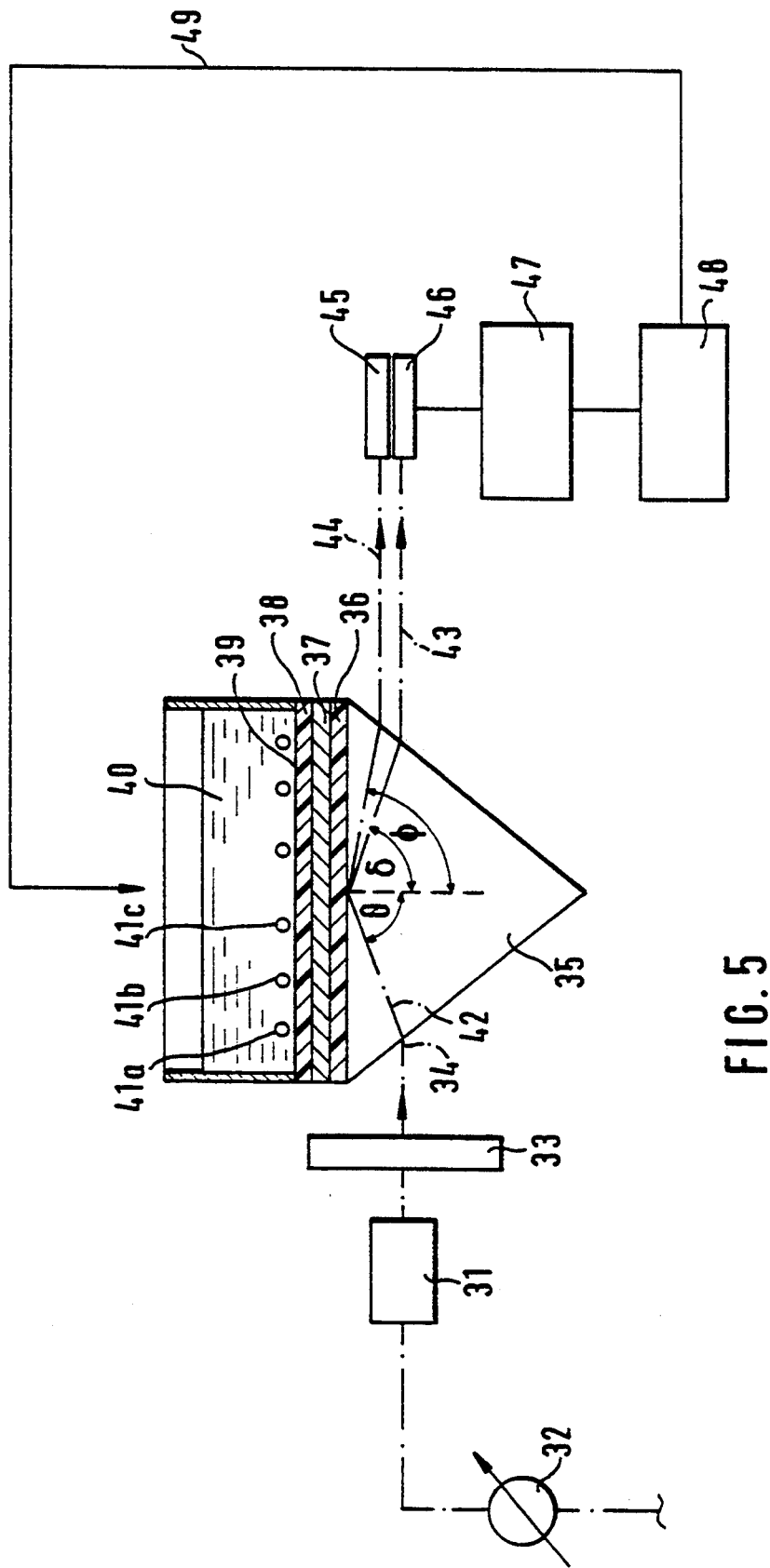
FIG. 5 is one embodiment of an apparatus according to the present invention.

In the embodiment of the invention shown in FIG. 5, the source of light 31 is adjustable, as indicated by control means 32. Control means 32 controls the energy output of light source 31, i.e., the intensity of the emitted beam. This beam is fed through a polarizer 33, in order to generate p-polarized light. Incident light beam 34 of p-polarized light then reaches glass prism 35.

In the embodiment of FIG. 5, three layers adjoin glass prism 35, namely a first dielectric layer 36, a metal layer 37 and a second dielectric layer 38. It has to be noted that the thickness of these layers is, as well as in the preceding figures, overdrawn for graphical purposes. In actuality, their thicknesses would only be several nanometers. Therefore, they form a boundary surface 39 to a solvent 40 containing target DNA and label DNA in solution, as described above. These DNA molecules adsorb to the boundary surface, also in the manner described above. Some adsorbed DNA molecules have been drawn for the purpose of illustration, see reference numbers 41a, 41b and 41c.

Light beam 42 impinges on the boundary surface at an angle of incidence $\theta$ (i.e., the angle between the incident light and the normal on the boundary surface). The angle of incidence $\theta$ is selected such that surface plasmon resonance occurs when, $\theta = \theta_{SPR}$.

However, it will be noted that there are two light rays 43, and 44 emerging from the point where the incident light beam hits the boundary surface.

Light ray 43 corresponds to excitation light reflected at the boundary surface. Angle $\delta$ of which light ray 43 is reflected equals the angle of incidence $\theta$, $\delta = \theta$.

Assuming the label DNA is labelled with a fluorescent label, then the surface plasmon wave excites the fluorescent labels and causes them to emit light of increased wavelength and decreased frequency, i.e., $\lambda_{emitted} > \lambda_{impinging}$ and $\nu_{emitted} < \nu_{impinging}$. ($\lambda$:Wavelength, $\nu$:Frequency). This is due to energy losses in the fluorescent molecules.

The light emitted by the fluorescent labels is coupled back into glass prism 35 by means of further surface plasmon wave (i.e., the emitted light generates a surface plasmon wave at the boundary surface, which in turn generates a light wave propagating through the glass prism). This is the light denoted as light beam 44 in FIG. 5. Due to the reduced frequency, its angle of reflectivity $\phi$ is different from the angle of incidence. Usually, the difference of angles $\delta$ and $\phi$ is only about 1° to 2°, i.e, $\phi - \delta \approx 1°$ to 2°.

Light rays 43 and 44 are detected by different detectors 45 and 46 (other embodiments will be discussed below). The intensity of the light ray received by detector 45 is used to determine the concentration of target DNA as is well known to those skilled in the art.

The output of detector 46 is fed to an intensity detector 47. A goal of the invention is to keep this intensity as low as possible by operating the apparatus optimally for surface plasmon resonance, i.e., $\theta = \theta_{SPR}$.

This step is performed by a control unit 48, which in turn controls the angle of incidence $\theta$ (feedback 49). The variation and control of the angle of incidence may be achieved in different ways; details will be discussed below.

FIG. 5 outlines the basic structure of an apparatus according to the present invention. A more detailed explanation will now be given with reference to FIG. 6.

Figure 6:
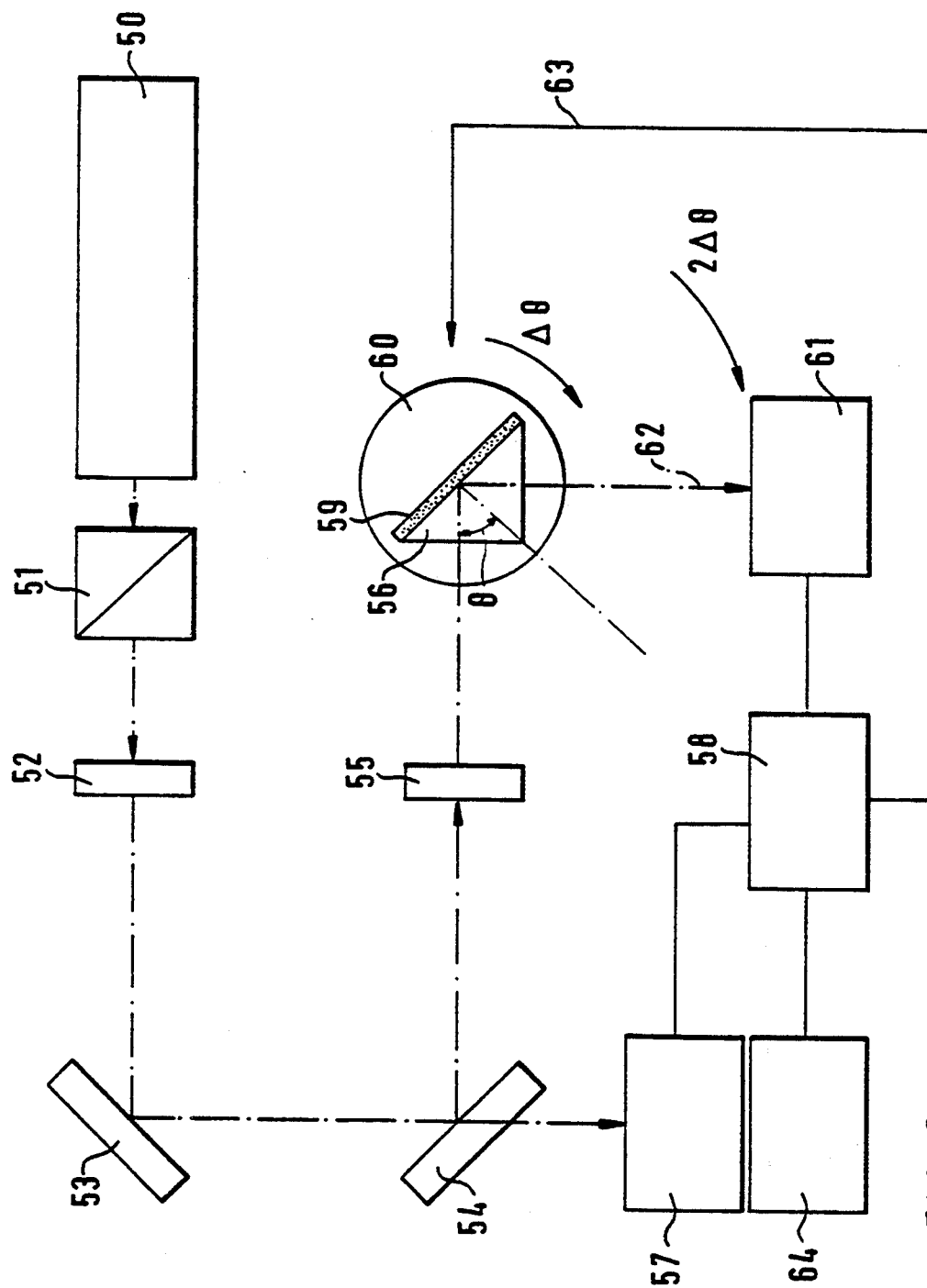
FIG. 6 depicts a second embodiment of an apparatus according to the present invention.

According to FIG. 6, light of a laser 50, e.g., a Helium-Neon laser, is fed to a polarizer 51 and further to an iris 52 (the iris is used to reduce stray light). A first mirror 53 and a second mirror 54 feed the impinging light further to a second iris 55 and to glass prism 56.

Mirror 54 is a semipermeable mirror. Some of the photons impinging on this mirror will not be reflected in the direction to iris 55, but pass mirror 54 instead. These photons hit a detector 57, which in turn is connected with a computer 58. The signal recorded by detector 57 is used as a reference signal, e.g., in order to control the energy of laser 50 or to normalize the measured DNA concentration.

The details of glass prism 56, and how target and label DNA adsorb to the boundary surface, are identical to that which was described in conjunction with FIG. 5 and will not be discussed here. The boundary surface with adsorbed DNA molecules is schematically indicated by reference number 59 in FIG. 6.

Glass prism 56 is mounted on a rotatable desk or table 60. One purpose of the rotation is to keep the angle of incident light $\theta$ at the optimum angle for surface plasmon resonance, i.e., $\theta = \theta_{SPR}$. The shaft of rotatable desk 60 is connected with suitable means for rotation, e.g., a stepper motor (not shown). Further, a transmission (e.g., with gear wheels) is provided which rotates a second detector 61 at twice the rate or angle at which rotatable desk 60 is rotated. For example, if rotatable desk 60 is rotated for an increment $\Delta\theta$, then detector 61 will be rotated for an increment $2*\Delta\theta$. Rotatable desks performing this function are known in the art and not explicitly shown here.

Detector 61 contains means for recording the light reflected at the boundary surface, as well as the light emitted by the fluorescent labels. It will be noted that no separate detectors (like in the environment of FIG. 5) are provided. Due to the small angular difference between these light beams, a single detector may be used. In fact, light ray 62 represents both light beams (the light reflected at the boundary surface, as well as the light emitted by the fluorescent labels).

The above-mentioned light beams are, however, easy to distinguish. One possibility is, for example, to use two detector elements in detector 61 having slight offsets in their angular positions. Another possibility is to use appropriate filters (one filter permitting the excitation light to pass, and the other adapted to the fluorescent wavelength). Advantageously, the filters may be operated in a time-multiplexed mode, such that a single detector receives the excitation light at a certain point in time, and the fluorescent wavelength at another point in time. Other arrangements will be known to those skilled in the art.

The signals detected by detector 61 are fed to computer 58, which uses the intensity of the reflected excitation light to control the drive means (e.g., stepper motor) of rotatable desk 60 to keep the angle of incidence $\theta$ at its optimum position for surface plasmon resonance, as indicated by feedback loop 63. The intensity of the fluorescent light is, in turn, used to calculate the concentration of DNA molecules at the boundary surface of glass prism 56. Computer 58 is further connected with a plotter 64, in order to record the results on paper.

Figure 7:
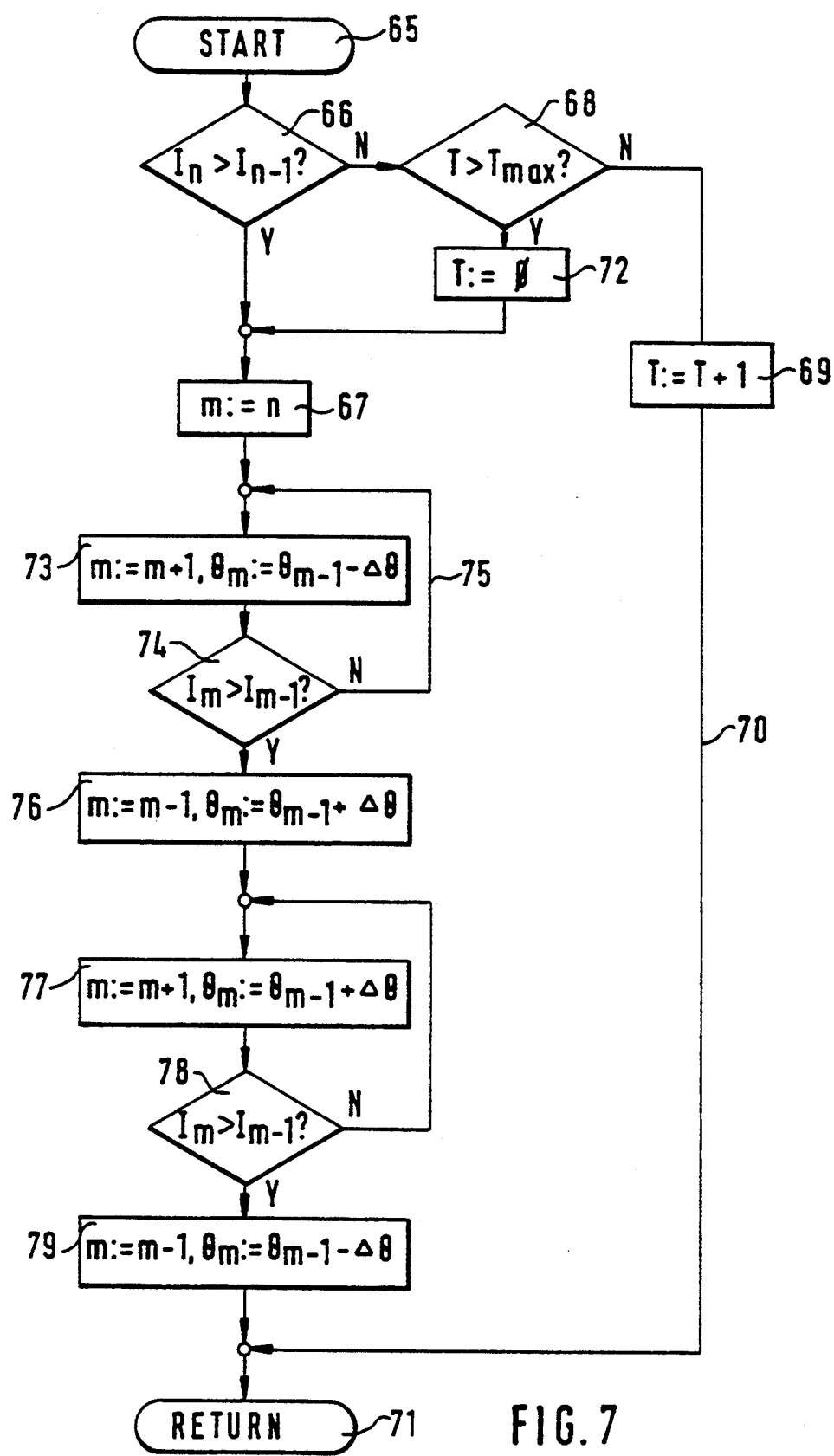
FIG. 7 is a flowchart for searching the intensity minimum of reflected light.

The flowchart of FIG. 7 depicts how the computer may keep the angle of incidence at its optimum position for surface plasmon resonance. The routine shown in FIG. 7 is processed in discrete time intervals and initiated by interrupts.

It is entered at label "START" (reference number 65). The routine first checks whether the intensity of the reflected excitation signal, $I_n$, is greater than the intensity $I_{n-1}$ measured the last time the flowchart was processed (reference number 66). If the answer is yes, this means that the apparatus is probably not operating at the optimum angle of incidence, and operation proceeds to box 67. It has to be noted that a possible increase of the intensity, i.e., $I_n > I_{n-1}$, does not necessarily mean that the angle of incidence is not at its optimum. The increase of intensity may have been caused by temperature effects, binding of unspecific molecules to the boundary surface, or the like, without shifting the optimum angle of incidence. However, there is a considerable probability that one of the above effects has caused the intensity minimum to move to another angle; likewise, the apparatus may simply be misadjusted.

If no increase of the intensity has been noted, it might still happen that the point of operation is not optimal. Assume, for example, that the level of minimum intensity has decreased, and that, at the same time, the minimum has been slightly shifted. In such case, the intensity at a certain point of operation may depict no increase or even a slight decrease, although this point of operation is no longer the point at which $\theta = \theta_{SPR}$.

The proposed routine, therefore, checks from time to time whether the present point of operation is still optimal, regardless whether there is any indication that the intensity has increased. This is shown by box 68. If the time since the last check, T, exceeds a preset value $T_{max}$, the next check is required. $T_{max}$ may, for example, be selected as several minutes or even hours.

If $T_{max}$ has not been exceeded, nor the intensity has increased, no readjustment is necessary. Operation proceeds to box 69 (increase of timer T) and then to the exit (line 70, "RETURN" label 71). Otherwise, timer T is set to zero (box 72).

In case a readjustment may be necessary, the routine scans the regions adjoining the present point of operation for new minima. This part of the routine starting with box 67 where a temporary counter m is set up (for the purpose of this part of the routine only).

In box 73, counter m is increased, and the angle of incidence $\theta$ is decreased by a preset value $\Delta\theta$ (e.g., corresponding to a single step of a stepper motor). With reference to FIG. 6, this may be a rotation of rotation desk 60 in clockwise direction.

The intensity at the new point of operation, $I_m$, is then compared with its previous value (reference number 74). If there is a decrease (line 75), this means that the present angle of incidence is nearer to the absolute minimum than its previous value, and rotation continues in the same direction.

If, however, the intensity at the new angle exceeds the intensity at the previous angle, the rotatable desk has been rotated too far. The last step is therefore corrected (box 76) by rotating the desk in the opposite direction.

In a similar manner, the angle of incidence is now increased (counterclockwise rotation of rotatable desk 60), step 77, in order to check whether there is any minimum in the other direction. Steps 78 and 79 correspond to steps 74 and 76.

It should be noted that, at the end of the routine, the angle of incidence may well correspond to the previous angle. This is, for example, the case when the search was initiated by expiration of timer T, but without any movement of the intensity minimum.

The flowchart in FIG. 7 depicts a quite simple routine to control the angle of incidence. More sophisticated programs may be developed by those skilled in the art, e.g., considering the derivative of the intensity, dI/dt, searching for a global minimum even in the presence of local minima.

Figure 8:
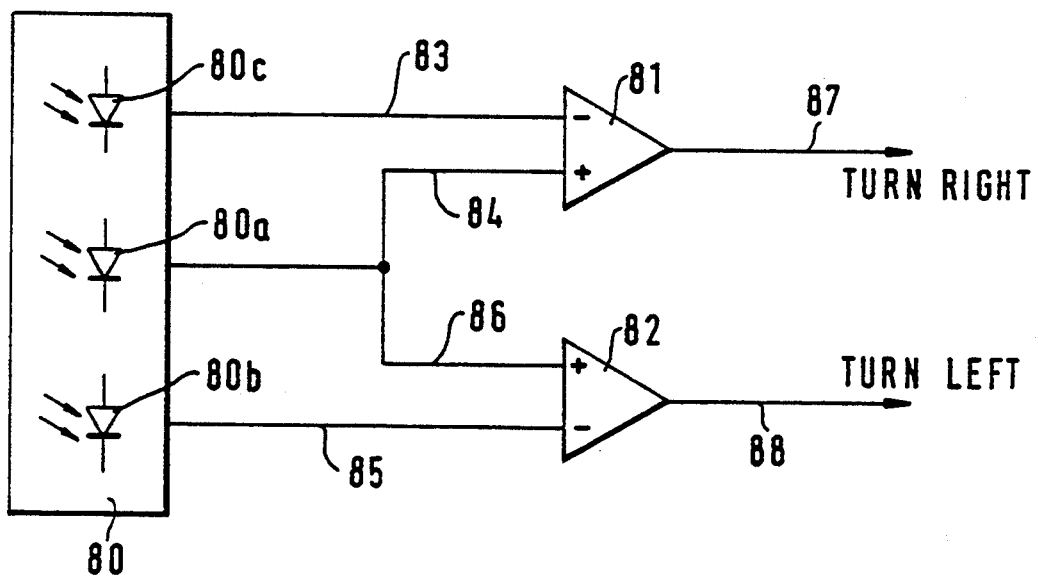
FIG. 8 depicts an alternative control mechanism based on a photodiode array.

Another possibility of controlling the angle of incidence is depicted in FIG. 8. A photodiode array 80 with a central photodiode 80a and two lateral photodiodes 80b and 80c receives the reflected excitation light. The photodiodes are slightly spaced with respect to each other.

The stray light received by photodiodes 80b and 80c represents a slightly different angle of incidence. As long as the central photodiode 80a receives the lowest intensity of all photodiodes, the apparatus operates at $\theta = \theta_{SPR}$, i.e. at its optimum condition. In such a case, comparators 81 and 82 will generate a negative or zero signal, which will not cause the stepper motor to rotate desk 60; i.e., nothing happens. Comparator 81 receives the intensity signal of photodiode 80c at its inverting input, line 83, and the intensity signal of photodiode 80a at its non-inverting input, line 84. Likewise, comparator 82 receives the intensity signal of photodiode 80b at its inverting input, line 85, and the intensity signal of photodiode 80a at its non-inverting input, line 86.

Assume now, for example, that the intensity at photodiode 80c is lower than the intensity indicated by central photodiode 80a. This means that the apparatus is misadjusted. Comparator 81 will now generate a positive control signal on line 87 in order to rotate the desk. If photodiode array 80 is part of detector 61 in FIG. 6, this means that the desk has to be rotated to the right or clockwise in order to decrease the angle of incidence. The intensity minimum will then be shifted to the center of photodiode array 80, i.e., in the direction of central photodiode 80a.

Rotation continues until central photodiode 80a records the minimum of intensity. In a similar manner, the desk is rotated counterclockwise via control line 88 if photodiode 80b records an intensity minimum.

FIG. 8 is only one example depicting the present invention. It is understood that, for example, the number of lateral photodiodes may be increased, and that light-sensitive elements other than photodiodes may be used.

While the invention has been described and illustrated with reference to specific embodiments, those skilled in the art will recognize that modification and variations may be made without departing from the principles of the invention as described hereinabove and set forth in the following claims.

What is claimed is:

1. A method for detecting biomolecules, comprising the steps of:
   (a) attaching a plurality of biomolecules to a boundary surface, said boundary surface being between an optically denser and an optically rarer medium and having a first side adjacent to said optically denser medium and a second side adjacent to said optically rarer medium, said plurality of biomolecules being attached by at least one of
      (i) adsorbing to said boundary surface;
      (ii) depositing on said boundary surface; and
      (iii) physically or chemically bonding to said boundary surface, said boundary surface having a film, the film having a conductive characteristic being capable of conducting surface plasmon waves, comprising the steps of:
   (b) irradiating p-polarized electromagnetic waves, using light through said optically denser medium onto said boundary surface, wherein the angle of incidence ($\theta$) of the p-polarized electromagnetic waves impinging onto said boundary surface is substantially equal to an angle ($\theta_{SPR}$) at which surface plasmon resonance occurs, surface plasmon waves capable of causing said plurality of biomolecules at said boundary surface to reflect or generate electromagnetic waves in response to said surface plasmon wave;
   (c) monitoring at least one of the electromagnetic waves reflected and the electromagnetic waves generated by said plurality of biomolecules at said boundary surface and determining at least one of:
      (i) the presence of said plurality of biomolecules; and
      (ii) the concentration of said plurality of biomolecules by analysis of at least one of said reflected or generated electromagnetic waves, wherein the intensity of the electromagnetic waves reflected or generated by said plurality of biomolecules at said boundary surface is detected; and
   (d) controlling the angle of incidence ($\theta$) of the impinging p-polarized electromagnetic waves depending on the intensity of reflected electromagnetic waves at said boundary surface such that said intensity is substantially maintained at a minimum corresponding to the occurrence of surface plasmon resonance.

2. The method according to claim 1, wherein said optically denser medium is a transparent prism.

3. The method according to claim 2, further comprising the step of:
   actuating a rotatable support carrying said transparent prism depending on said intensity.

4. The method according to claim 3, wherein said rotatable support is rotated in a first direction and then in a second direction opposite to said first direction in response to an increase in said intensity, or in case a predetermined time period ($T_{max}$) has expired.

5. The method according to claim 1, wherein said electromagnetic waves reflected at said boundary surface are fed to an array of monitoring elements comprising at least a central monitoring element and at least a lateral element at either side of said central monitoring element and a control signal causing adjustment of said angle of incidence ($\theta$) is generated if the intensity detected by one of said lateral elements is lower than the intensity detected by said central element.

6. The method according to claim 1, further comprising at least one of:
   (i) passing p-polarized electromagnetic waves through a dielectric layer before passing through said film, and
   (ii) passing p-polarized electromagnetic waves through a dielectric layer after passing through said film.

7. The method according to claim 1, wherein said optically rarer medium is a solvent in which said plurality of biomolecules are dissolved such that at least some of said plurality of biomolecules adsorb to, deposit on, or are physically or chemically bound to said second side of said boundary surface.

8. The method according to claim 7, wherein at least one of said plurality of biomolecules and complementary biomolecules which are complementary to said plurality of biomolecules are labelled with a fluorescent, phosphorescent, chemiluminescent or electroluminescent substance.

9. The method according to claim 8, wherein said second side of said boundary surface is coated with capture molecules complementary to said plurality of biomolecules, said solvent comprising said plurality of biomolecules and labelled biomolecules complementary to said biomolecules.

10. The method according to claim 9, wherein said second side of said boundary surface is coated with capture molecules complementary to said plurality of biomolecules, said solvent comprising said plurality of biomolecules and labelled biomolecules complementary to said biomolecules.

11. The method according to claim 1, wherein at least one of said plurality of biomolecules and complementary biomolecules which are complementary to said plurality of biomolecules are labelled with a fluorescent, phosphorescent, chemiluminescent or electroluminescent substance.

12. The method according to claim 1, wherein said optically rarer medium is a solvent in which said plurality of biomolecules are dissolved such that at least some of said plurality of biomolecules adsorb to, deposit on, or are physically or chemically bound to said second side of said boundary surface.

13. The method according to claim 12, wherein at least one of said plurality of biomolecules and complementary biomolecules which are complementary to said plurality of biomolecules are labelled with a fluorescent, phosphorescent, chemiluminescent or electroluminescent substance.

14. An apparatus for detecting biomolecules at a boundary surface, said boundary surface being between an optically denser medium and an optically rarer medium, said biomolecules being attached on or to said boundary surface, and said boundary surface having a film with a conductive characteristic coupled thereto, said film being capable of conducting surface plasmon waves, the apparatus comprising:
   a source of electromagnetic waves;
   polarizing means for p-polarizing the electromagnetic waves emitted by said source of electromagnetic waves;
   means for directing said p-polarized electromagnetic waves through an optically denser medium onto said boundary surface, said boundary surface being between said optically denser medium and an optically rarer medium;
a first monitoring means for monitoring radiation reflected or generated by said biomolecules at said boundary surface;
a second monitoring means for monitoring electromagnetic waves reflected at said boundary surface;
an intensity detection means coupled to said first and second monitoring means for detecting an intensity of said electromagnetic waves reflected at said boundary surface; and
a control means coupled to said intensity detection means and coupled to said means for directing said p-polarized electromagnetic waves, said control means controlling the angle of incidence of the impinging p-polarized electromagnetic waves depending on the intensity of the electromagnetic waves reflected at said boundary surface such that said intensity is substantially maintained at a minimum corresponding to an occurrence of surface plasmon resonance.

15. The apparatus according to claim 14, wherein said second monitoring means comprises a detector, the detector being responsive only in the spectrum of said p-polarized electromagnetic waves.

16. The apparatus according to claim 14, wherein said first monitoring means together with said second monitoring means comprise a detector selectively responsive to said p-polarized electromagnetic waves and said electromagnetic waves reflected at said boundary surface.

17. The apparatus according to claim 14, wherein said second monitoring means comprises an array of monitoring elements, with at least a central monitoring element and at least a lateral element at either side of said central monitoring element, a control signal generating means are providing a control signal if the intensity detected by one of said lateral elements is lower than the intensity detected by said central monitoring element, said control signal being fed to said control means.

18. The apparatus according to claim 14, wherein said means for directing said p-polarized electromagnetic waves onto the boundary surface comprises a transparent prism.

19. The apparatus according to claim 18, wherein said transparent prism is mounted on a support rotatable by operating means, controlled by said control means, wherein said transparent prism is rotated an angle ($\Delta\theta$).

20. The apparatus according to claim 19, further comprising:
transmission means for rotating said support around first angle ($\theta$) and for rotating at least one of said first and second monitoring means twice said first angle ($2\Delta\theta$).

21. The apparatus according to claim 14, wherein said source of electromagnetic waves is adjustable.

22. A method for detecting biomolecules, comprising the steps of:
(a) attaching a plurality of biomolecules to a boundary surface, said boundary surface being between an optically denser and an optically rarer medium and having a first side adjacent to said optically denser medium and a second side adjacent to said optically rarer medium, said plurality of biomolecules being attached by at least one of
(i) adsorbing to said boundary surface;
(ii) depositing on said boundary surface; and
(iii) physically or chemically bonding to said boundary surface, said boundary surface having a film, the film having a conductive characteristic being capable of conducting surface plasmon waves;
(b) irradiating said plurality of biomolecules so attached to said boundary surface with impinging electromagnetic waves so that said impinging electromagnetic waves pass through said optically denser medium onto said boundary surface, wherein the angle of incidence ($\theta$) of the impinging electromagnetic waves is substantially equal to an angle ($\theta_{SPR}$) at which surface plasmon resonance occurs, surface plasmon waves capable of causing said plurality of biomolecules at said boundary surface to at least reflect or generate electromagnetic waves in response to said surface plasmon wave;
(c) detecting the intensity of at least one of the electromagnetic waves reflected and the electromagnetic waves generated by said plurality of biomolecules at said boundary surface;
(d) determining based upon said intensity so detected at least one of:
(i) the presence of said plurality of biomolecules; and
(ii) the concentration of said plurality of biomolecules; and
(e) monitoring shifts in the angle $\theta_{SPR}$ by detecting the intensity of the reflected electromagnetic waves;
(f) controlling the angle of incidence ($\theta$) of the impinging p-polarized electromagnetic waves depending on the intensity of reflected electromagnetic waves so detected to substantially optimize the energy of the impinging p-polarized electromagnetic waves coupled into said plurality of biomolecules for making said determination of step (d).

23. The method according to claim 22, wherein said optically denser medium is a transparent prism.

24. The method according to claim 22, further comprising the step of:
actuating a rotatable support carrying said transparent prism depending on said intensity.

25. The method according to claim 24, wherein said rotatable support is rotated in a first direction and then in a second direction opposite to said first direction in response to an increase in said intensity, or in case a predetermined time period ($T_{max}$) has expired.

26. The method according to claim 22, wherein said electromagnetic waves reflected at said boundary surface are fed to an array of monitoring elements comprising at least a central monitoring element and at least a lateral element at either side of said central monitoring element and a control signal causing adjustment of said angle of incidence ($\theta$) is generated if the intensity detected by one of said lateral elements is lower than the intensity detected by said central element.

27. The method according to claim 22, further comprising at least one of:
(i) passing said impinging electromagnetic waves through a dielectric layer before passing through said film, and
(ii) passing impinging electromagnetic waves through a dielectric layer after passing through said film.

28. The method according to claim 22, wherein at least one of said plurality of biomolecules and complementary biomolecules which are complementary to said plurality of biomolecules are labelled with a fluorescent, phosphorescent, chemiluminescent or electroluminescent substance.

29. An apparatus for detecting biomolecules at a boundary surface, said boundary surface being between an optically denser medium and an optically rarer medium, said biomolecules being attached on or to said boundary surface, and said boundary surface having a film with a conductive characteristic coupled thereto, said film being capable of conducting surface plasmon waves, the apparatus comprising:

a source of electromagnetic waves;

polarizing means for p-polarizing the electromagnetic waves emitted by said source of electromagnetic waves;

means for directing said p-polarized electromagnetic waves through an optically denser medium onto said boundary surface to effect surface plasmon resonance whereby energy is coupled into said biomolecules, said boundary surface being between said optically denser medium and an optically rarer medium and having a first side adjacent to said optically denser medium and a second side adjacent to said optically rarer medium;

a first monitoring means for monitoring radiation reflected or generated by said biomolecules at said boundary surface to determine at least one of a presence and a concentration of said biomolecules;

an intensity detection means coupled to said first monitoring means for detecting an intensity of said electromagnetic waves reflected at said boundary surface;

a second monitoring means coupled to said intensity detection means for monitoring, based on said intensity, a shift in an angle of incidence at which surface plasmon resonance occurs ($\theta_{SPR}$); and a control means coupled to said second monitoring means and coupled to said means for directing said p-polarized electromagnetic waves, said control means controlling the angle of incidence ($\theta$) of the impinging p-polarized electromagnetic waves depending on the intensity of the electromagnetic waves reflected at said boundary surface to substantially optimize the energy of the impinging p-polarized electromagnetic waves coupled into said biomolecules for said determination of said presence or concentration of said plurality of biomolecules.

30. The apparatus according to claim 29, wherein said second monitoring means comprises a detector, the detector being responsive only in the spectrum of said p-polarized electromagnetic waves.

31. The apparatus according to claim 29, wherein said intensity detection means comprises an array of detection elements, with at least a central detection element and at least a lateral detection element at either side of said central detection element, said second monitoring means monitoring said intensity detected at said detection elements and providing a control signal if the intensity detected by one of said lateral elements is lower than the intensity detected by said central monitoring element, said control signal being fed to said control means.

32. The apparatus according to claim 29, wherein said means for directing said impinging electromagnetic waves onto said boundary surface comprises a transparent prism.

33. The apparatus according to claim 32, wherein said transparent prism is mounted on a support rotatable by operating means, controlled by said control means, wherein said transparent prism is rotated an angle ($\Delta\theta$).

34. The apparatus according to claim 33, further comprising:

transmission means for rotating said support around angle ($\Delta\theta$) and for rotating at least one of said first and second monitoring means twice said angle ($2\Delta\theta$).

* * * * *